United States Patent [19]
Ence

[11] Patent Number: 6,122,054
[45] Date of Patent: *Sep. 19, 2000

[54] DEVICE FOR MEASURING THE CONCENTRATION OF AIRBORNE FIBERS

[75] Inventor: Brian Miller Ence, Lansdale, Pa.

[73] Assignee: CertainTeed Corporation, Valley Forge, Pa.

[ * ] Notice: This patent is subject to a terminal disclaimer.

[21] Appl. No.: 09/071,818

[22] Filed: May 1, 1998

Related U.S. Application Data

[63] Continuation-in-part of application No. 08/743,554, Nov. 4, 1996, Pat. No. 6,005,662, and a continuation-in-part of application No. 08/743,555, Nov. 4, 1996.

[51] Int. Cl.[7] .................................................... G01N 21/00
[52] U.S. Cl. ............................................ 356/338; 356/343
[58] Field of Search ..................... 356/338, 336, 356/343

[56] References Cited

U.S. PATENT DOCUMENTS

| | | | |
|---|---|---|---|
| 4,473,296 | 9/1984 | Shofner et al. | 356/336 |
| 4,737,648 | 4/1988 | Smith et al. | 356/343 |

*Primary Examiner*—Robert H. Kim
*Attorney, Agent, or Firm*—Duane Morris & Heckscher LLP

[57] ABSTRACT

Devices and methods for measuring the concentration of airborne fibers are provided. The devices include flow means for providing laminar flow to a portion of the fibers in an air sample and a light source for generating a light beam directed to the laminarly flowing fibers to produce a scattered light. The device further includes a sensor for sensing a portion of this scattered light and for producing an output from which a respirable fiber concentration estimate can be measured.

20 Claims, 8 Drawing Sheets

DEVICE FOR MEASURING THE CONCENTRATION OF AIRBORNE FIBERS

CROSS-REFERENCE TO RELATED APPLICATION

This application is a continuation-in-part application of U.S. patent application Ser. No. 08/743,554, entitled "Device For Measuring The Dimension Of A Airborne fiber", filed on Nov. 4, 1996, now U.S. Pat. No. 6,005,662 and U.S. patent application Ser. No. 08/743,555, filed on Nov. 4, 1996, which applications are assigned to the same assignee hereof, and are hereby incorporated by reference.

FIELD OF THE INVENTION

This invention relates to methods and devices for estimating the concentration of airborne fibers, and particularly to devices which can decipher between respirable fibers and non-fibrous respirable fibers.

BACKGROUND OF THE INVENTION

At present, two primary methods for monitoring airborne fiber concentration exist. In the first method, airborne fibers are collected on a filter. This filter is analyzed by microscopy or chemical methods to determine the type of fibers present and to estimate airborne fiber concentration. This method suffers from the drawbacks of delayed availability of information, tediousness, inconvenience, high cost per sample, and lack of precision. Also, identification of fibers typically is performed by visual inspection, adding uncertainty to measurements for particular species of airborne fibers.

In the second method, real-time airborne fibers concentration is determined using optical techniques, in which light, attenuated by fibers passing by a light source, is analyzed. However, most of these devices do not discriminate between different species of airborne fibers and, in particular, may not provide an accurate measurement of potentially respirable fibers, particularly small glass fibers.

Because of the significant health problems posed by airborne asbestos fibers, current real-time airborne fiber monitors typically are aimed at selectively determining asbestos fiber concentration in an air sample having asbestos and other fibers. Because asbestos fibers exhibit paramagnetic properties, some existing devices preferentially align and oscillate asbestos fibers using, for example, a time-varying electric field quadruple, a hybrid electric/magnetic field, or both. The induced oscillations tend to create a characteristic scattering of an impinging light, thus identifying the oscillating fiber as asbestos. Electrostatic techniques also may be used. Examples of such devices and methods for measuring airborne particulate concentration are found in U.S. Pat. No. 3,692,412 to Chubb (1972), entitled "Apparatus for Analyzing Suspended Particles"; in U.S. Pat. No. 4,940,327, to Lillienfeld (1990), entitled "Method and Apparatus for Real-Time Asbestos Monitoring"; and in U.S. Pat. No. 5,319,575, also to Lillienfeld (1994), entitled "System and Method for Determining and Outputting Airborne Particle Concentration." Also see MIE Fiber Monitor Model FM-7400 User's Manual by MIE, Inc., Billerica, Mass.

However, because potentially harmful respirable fibers including, for example, glass fibers, often do not exhibit paramagnetism, such methods may not be appropriate. What is needed, then, is an airborne fiber concentration measuring device that can accurately determine the concentration of respirable fibers suspended in an air sample, in real time, without the need for electrostatic, magnetic or hybrid electromagnetic components.

Additionally, the Lillienfeld's device is more complicated, detects only a ;mall percentage of fibers in a given sample, and if the concentration of fibers in the sample is low or not representative of the fiber concentration in the air flow, measurement errors can result. There therefore remains a need for a fiber concentration measuring device which takes a more significant sampling of the fiber population and which is accurate at low concentration readings.

SUMMARY OF THE INVENTION

This invention provides devices and methods for measuring the concentration of airborne fibers in a fiber-containing air sample. The preferred device includes flow means for providing laminar flow to at least a portion of the fibers in the air sample. These laminarly flowing fibers are then illuminated with a light source to produce scattered light. A portion of the scattered light is then sensed to produce an output from which a fiber concentration estimate can be measured. Additionally, separation devices can be used to preselect fibers having a particular size, so as to measure only respirable fibers, for example. This invention provides an inexpensive way of measuring respirable fibers in a work environment, such as a glass insulation or mat-making facility.

In a more detailed embodiment of this invention, a device is provided for analyzing air having respirable fibers, and non-respirable fibers or non-fibrous particulate matter, or both. This device includes separation means for selectively removing respirable fibers from non-respirable fibers to produce a filtered air sample containing aligned respirable fibers. These aligned fibers are then illuminated to produce scattered light, which is collected by a light sensor to produce an electrical output. The device further includes processing means for providing a concentration estimate for the respirable fibers from the output of the light sensor.

This invention also provides improvements in fiber illumination techniques, and concentration measurement detection. As a result of improved beam patterns, the signals created when a fiber passes through the beam are more closely related to the diameter of the fiber. Given that the signal from a fiber is related to its diameter it is possible to discriminate between respirable and non-respirable fibers electronically. Hence for certain improved versions of this invention the virtual impactor is removed and additional pulse discriminating and counting electronics are added. Such modifications include two or more circuits for detecting and counting pulses. One circuit counts all pulses above a certain minimum threshold level in a given period of time. These counts represent all of the fibers that passed through the laser beam. The added circuit counts only the pulses above a preselected upper threshold level diameter during the same period. These counts represent fibers that have a larger non-respirable diameter. Subtracting the counts of the second circuit from the first gives the number of respirable fibers that passed through the beam. Having computed the number of respirable fibers that passed through the beam the concentration of fibers per unit volume can be determined based on the duration of the counting period and the air flow rate through the sensor.

BRIEF DESCRIPTION OF THE DRAWINGS

The accompanying drawings, referenced to herein and constituting a part hereof, illustrate preferred embodiments of the device of the present invention and, together with the description, serve to explain the principles of the invention.

DETAILED DESCRIPTION OF THE INVENTION

Fiber Concentration Measurements

Figure 1:
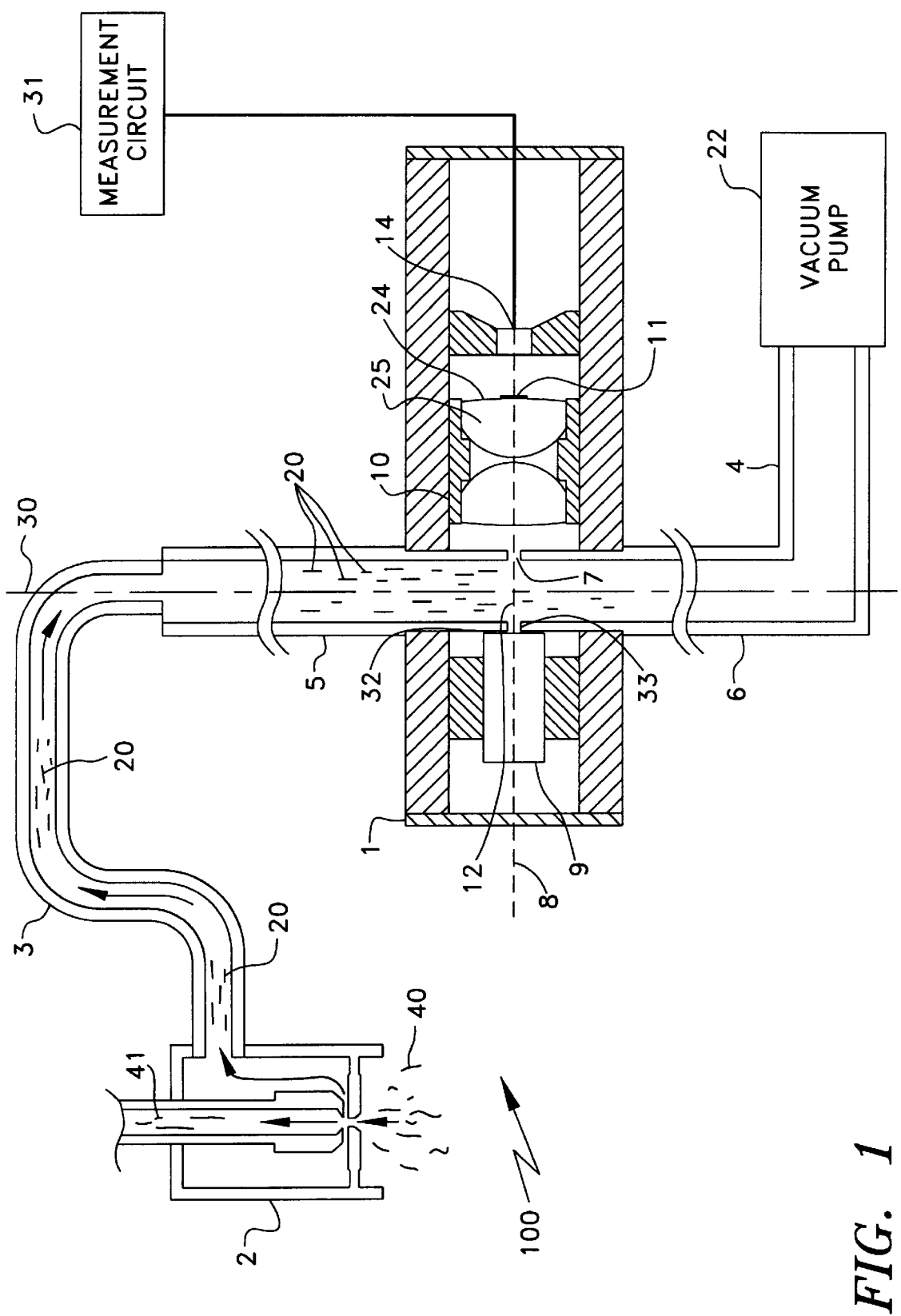
FIG. 1 is an illustration of an airborne fiber concentration measuring device in accordance with the present invention.

FIG. 1 illustrates one embodiment of the airborne fiber concentration measuring device 100 according to the principles of the invention herein. Device 100 can include at sensor 1 for detecting fibers and separation means, for example, virtual impactor 2, for separating respirable from non-respirable fibers or non-fibrous particulate matter. As used herein, "respirable fibers" means fibers which are less than about 3 $\mu$M in diameter, and preferably those with an aspect ratio of at least about 5:1 (length:diameter). Additionally, the term "light" refers to both visible and invisible electromatic waves, including x-ray and infrared.

A skilled artisan would recognize that virtual impactor 2 can use well-known techniques to separate the respirable particles from non-respirable particles, and therefore, the skilled artisan could employ other separating means for isolating respirable fibers from non-respirable fibers. One exemplary virtual impactor 2 that has been found suitable is shown in FIG. 1. This device takes in fiber-containing ambient air and draws off smaller respirable fibers 20 laterally at a venturi's mouth. Larger fibers 41, greater than about 3 $\mu$m, are drawn into the center tube of the virtual impactor 2.

In general, the air entering the device can have respirable fibers, non-respirable fibers, and other particulate matter mixed therein. Sensor 1 preferably senses aligned respirable fibers in the air but is substantially insensitive the other non-fibrous particulate matter. In operation, respirable fibers 20 that may be present in the air are drawn from virtual impactor 2 through hose 3 which connects virtual impactor 2 to sensor 1. Air is drawn through the system by a small vacuum pump 22 to outlet 4 of lower flow tube 6. The air flow rate, and lengths and diameter of the upper and lower flow tubes 5,6, are preferred to be such as to produce a laminar flow of air through tubes 5,6. This laminar airflow tends to cause the fibers 20 in the air within tubes 5,6 to become substantially aligned with the airflow and, hence, with the longitudinal axis 30 of flow tubes 5,6. Flow tubes 5,6 preferably are separated by a small gap 7 within sensor 1. Alternatively, a single tube having a pair of slots through its side wall perpendicular to its axis could work as well. This gap 7 is preferably positioned symmetrically about axis 8 of sensor 1. Flow tubes 5,6 and gap 7 constitute the "flow channel" for this embodiment of the invention.

Within sensor 1 is a light source 9 which can be a coherent light source such as, for example, a diode laser, such as a focusable diode laser Model No. 5NF-501L-670-5-10, available from Lasiris, Inc., Fairport, N.Y. Light source 9 can produce a thin narrow light beam 12, preferably with a preselected cross-section along the beam path. It is preferred that light source 9 produce a collimated beam of light, ideally with an elliptical cross-section directed at light sensor 14. Light sensor 14 is preferred to be a photodetector. Beam 12 can be aimed along axis 8 of sensor 1 with the major axis of the ellipse of light preferably being substantially parallel to gap 8 between flow tubes 5,6. The width of beam 12 need not be as wide as the diameter of flow tubes 5,6.

A suitable light source for this embodiment can be, for example, a model LPM 03(670-5) laser diode from Power Technology, Inc., Little Rock, Ark. Similarly, a suitable photodetector is, for example, Devar Model 509-1, Bridgeport, Conn. A skilled artisan could employ other suitable light sources and light sensors to provide and detect light signals indicative of the presence of respirable fiber.

FIG. 2 presents a cross-sectional view of a preferred sensor 1, which is positioned generally perpendicular to the airflow. After passing through gap 7, beam 12 enters an optical lens assembly 10. Lens assembly 10 can be a pair of condensing lenses, for example. This combination of lenses tends to have a short focal length, permitting a portion 23 of beam 12 to be directed to the back surface 24 of the second lens 25. Beam block 11 can be used to substantially block the collimated light 23 from being sensed by photodetector 14. It is preferred that the beam block 11 be umbrageously situated relative to photodetector 14 so that beam block 11 can shield photodetector 14 from light not indicative of the presence of a sensed fiber.

As fibers 20 pass though the beam 12 between the flow tubes 5,6, some of the fibers 20 will scatter the light, as shown in FIG. 2. When a cylinder, such as a glass fiber, is illuminated at a normal incidence by light, it typically scatters the light in a preselected orientation in the flow channel, i.e. in a plane that is normal to the cylinder. Because fibers 20 have been aligned by the laminar airflow, these fibers 20 are generally oriented perpendicularly to the direction of beam 12. Therefore, beam 12 can be scattered in a plane that is generally parallel to planes formed by the ends of flow tubes 5,6, thus permitting scattered light 26 to pass through gap 7 between flow tubes 5,6.

For the laminar flow of this invention it is generally recognized that two conditions must be met. These are that the Reynolds number should be less than about 2000 and there must be sufficient distance for the flow to become laminar. In the case of the claimed device, a flow of about 4 liters/min. and a fiber diameter of 0.44 in. (1.1 cm) produces a Reynolds member of about 500, which is well into the laminar flow regime. The length of the flow tube before the fibers reach the laser beam is about 5–50 in. (12.7–127 cm), preferably about 10 in. (25.4 cm) which is more than 22 times the fiber diameter. Since laminar flow should develop within 10 diameters from the entrance of the tube the flow in the device should have ample time to assume a laminar condition.

A visual confirmation of the alignment of fibers during the transition between turbulent flow and laminar flow can be made. It can be seen that: in the case of glass fibers in a turbulent flow, the diffracted laser beam is dispersed into separated spots of light in random directions; while in the case of glass fibers in a laminar flow, the diffracted laser beam is concentrated in approximately one direction (area), thus showing that the fibers are aligned in a direction substantially parallel to the flow.

Light that is scattered in a forward direction 13 can be collected by lens assembly 10 and focused on photodetector 14. Because this light typically is not collimated when it enters the lens assembly 10, it can be focused to a point some distance beyond lens assembly 10, thereby passing around beam block 11. Thus, while both the beam 12 and scattered light 26 enter lens assembly 10, beam 12 typically is blocked from impinging on photodetector 14 while scattered light 26 is, for the most part, focused onto the photodetector 14. Overall, only a small fraction of scattered light 26 is blocked by beam block 11.

It is preferred that photodetector 14 have a sensing region with a finite width which is wide enough to receive the scattered light 26. Within this width, it will respond to light scattered by fibers 20 that are some distance to either side of, as well as in front and in back of, axis 30 of flow tubes 5,6. Therefore, fibers 20 are not required to pass through beam 12 single-file or closely aligned with axis 30. When beam 12 is scattered by fiber 20, it is focused though lens assembly 10 to impinge upon photodetector 14, thus generating a brief electrical pulse therefrom. In general, the amplitude of this pulse is preferred to be proportional to the amount of light scattered by the fiber. The resultant pulse can be sent to an appropriate electronic measurement circuit 31 where the pulse is recorded. Using other quantitative information, such as, the flow rate of the air through sensor 1, and determining the rate at which the pulses are received, the concentration of respirable fibers in the air can be determined.

It is preferred that sensor 1 be substantially insensitive to non-fibrous particulate matter. Presently preferred embodiment of the current invention accomplish this selectivity by analyzing, for example, the optical differences between the typically cylindrical respirable fibers, and particulate matter having other shapes. That is, if a spherical or irregularly-shaped dust particle is drawn into sensor 1, the particulate matter will also scatter light from beam 12. However, such a particle tends to scatter light into a spherical volume. Much of this scattered light will impinge on, and be absorbed by the walls of flow tubes 5,6.

In general, only a small fraction of the light scattered by these particles tends to pass through the gap 7 between flow tubes 5,6. This small amount of scattered light tends to produce only a weak signal in photodetector 14. Circuit 31, receiving pulses from the photodetector 14, can be designed to ignore low amplitude pulses resulting from particulate matter. Therefore, device 100 can be made to respond only to respirable fibers while ignoring other non-fibrous particulate matter that may be present. Unlike prior art devices, the invention herein does not require the use of electrostatic or electromagnetic components to induce movement in the matter suspended in the air in order to determine whether or not the matter is a respirable fiber.

Indeed, the ability of device 100 to discriminate between respirable fibers and other particles could optionally use the following principles. First, non-respirable fibers are eliminated from the airflow by separation means, i.e. virtual impactor 2, before the air enters sensor 1. Second, the remaining fibers tend to be aligned with flow tube axis 30 by the laminar flow of air through tubes 5,6. Third, beam 12 generally is oriented to be normal to the axis of tubes 5,6. Fourth, light scattered by fibers 20 tends to be scattered in a plane which passes between the ends of flow tubes 5,6, and a portion of the scattered light is focused onto photodetector 14. Fifth, light scattered by other particles tends to be scattered more omni-directionally than is the case with cylinders. Most of this light is absorbed by the walls of flow tubes 5,6 and only a small amount of light remains to be focused on photodetector 14. Sixth, by discriminating between the amplitude of signals received from photodetector 14, device 100 can discriminate between fibers and other particles.

Figure 2:
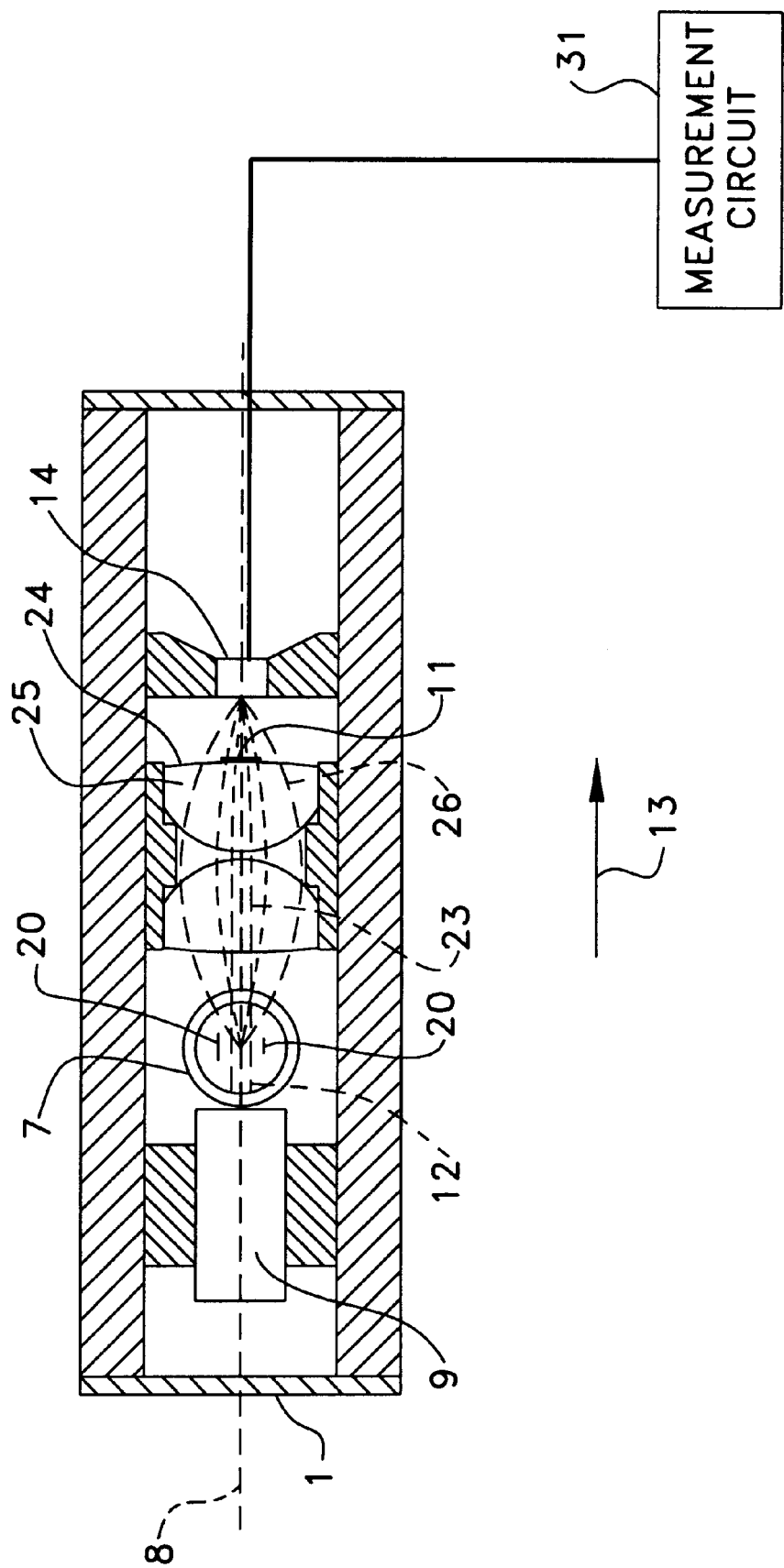
FIG. 2 is an illustration of one presently preferred embodiment of a sensor in accordance with the present invention.

In FIGS. 1 and 2, lens assembly 10 and photodetector 14 are shown as being substantially in-line with, or in opposition to, beam 12. In view of the teachings of this invention, a skilled artisan would recognize that lens assembly 10 and photodetector 14 may be placed anywhere around axis 30 of flow tubes 5,6, as long as they are still in the plane of light scattered from fibers 20. Although the amount of light collected by lens assembly 10 can depend upon the location of lens assembly 10, sensor 1 can discriminate between respirabole fibers and other particles even with these alternative configurations.

Figure 3:
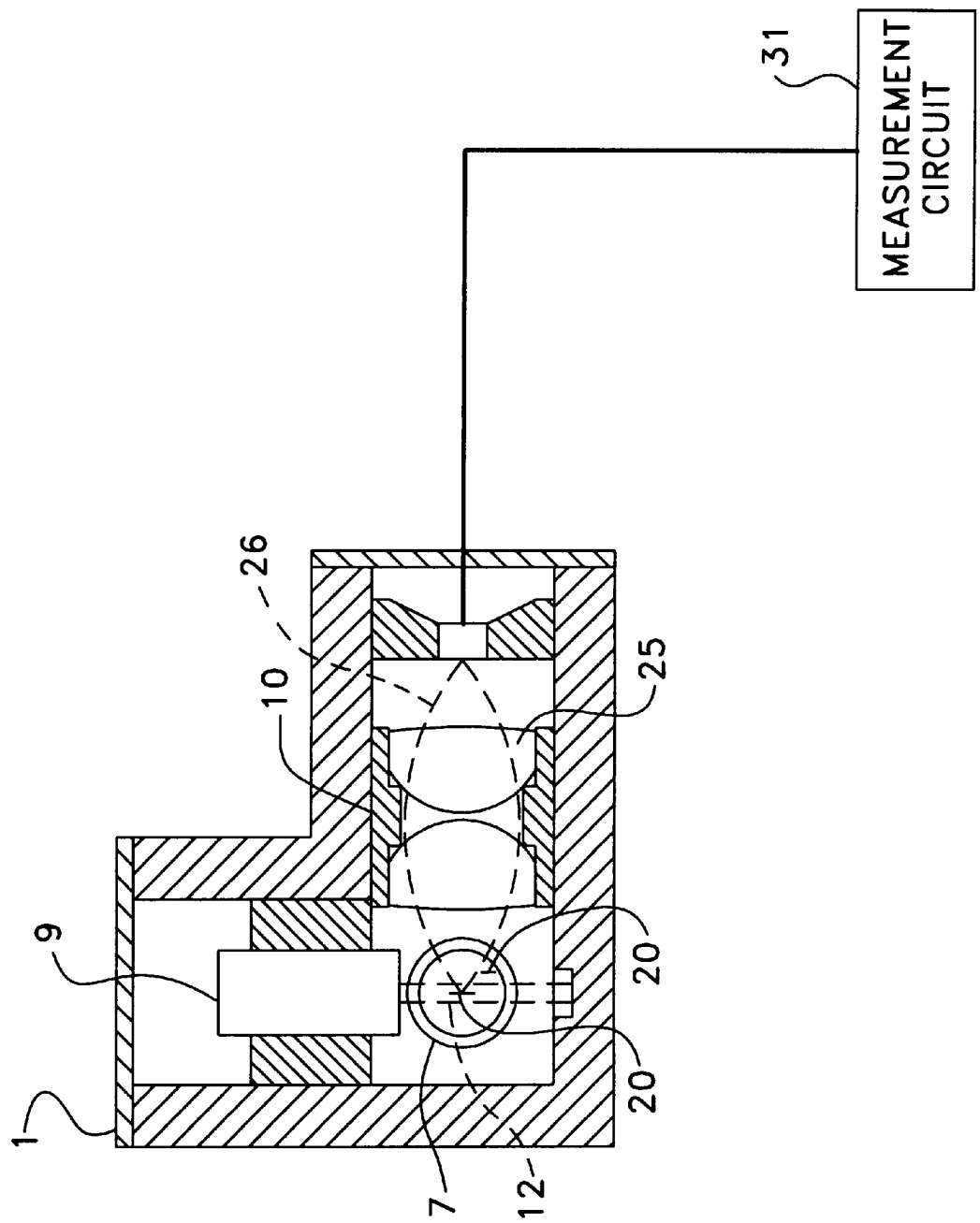
FIG. 3 is an illustration of another presently preferred embodiment of a sensor in accordance with the present invention.

In FIG. 3, for example, the components of device 100 are substantially the same as those in FIGS. 1 and 2, with the exception that lens assembly 10 and photodetector 14 have been rotated in orientation by 90 degrees. Also in FIG. 3, beam block 11 seen in FIGS. 1 and 2, may be eliminated because beam path 12 no longer is in-line with, or in opposition to, photodetector 14.

Fiber Diameter Measurements

Figure 4:
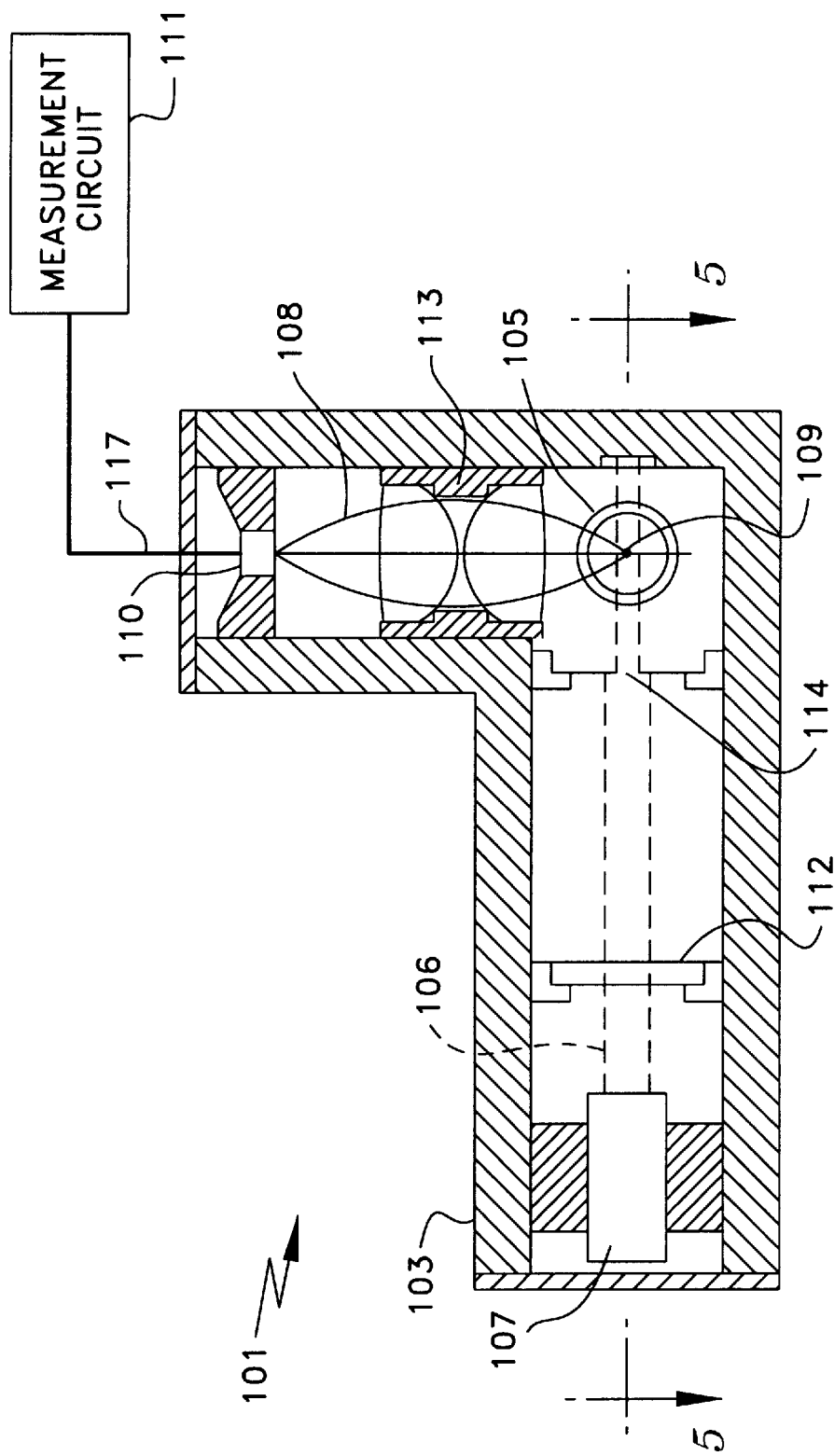
FIG. 4 is a front, cross-sectional illustration of a fiber diameter measuring device of this invention.
Figure 5:
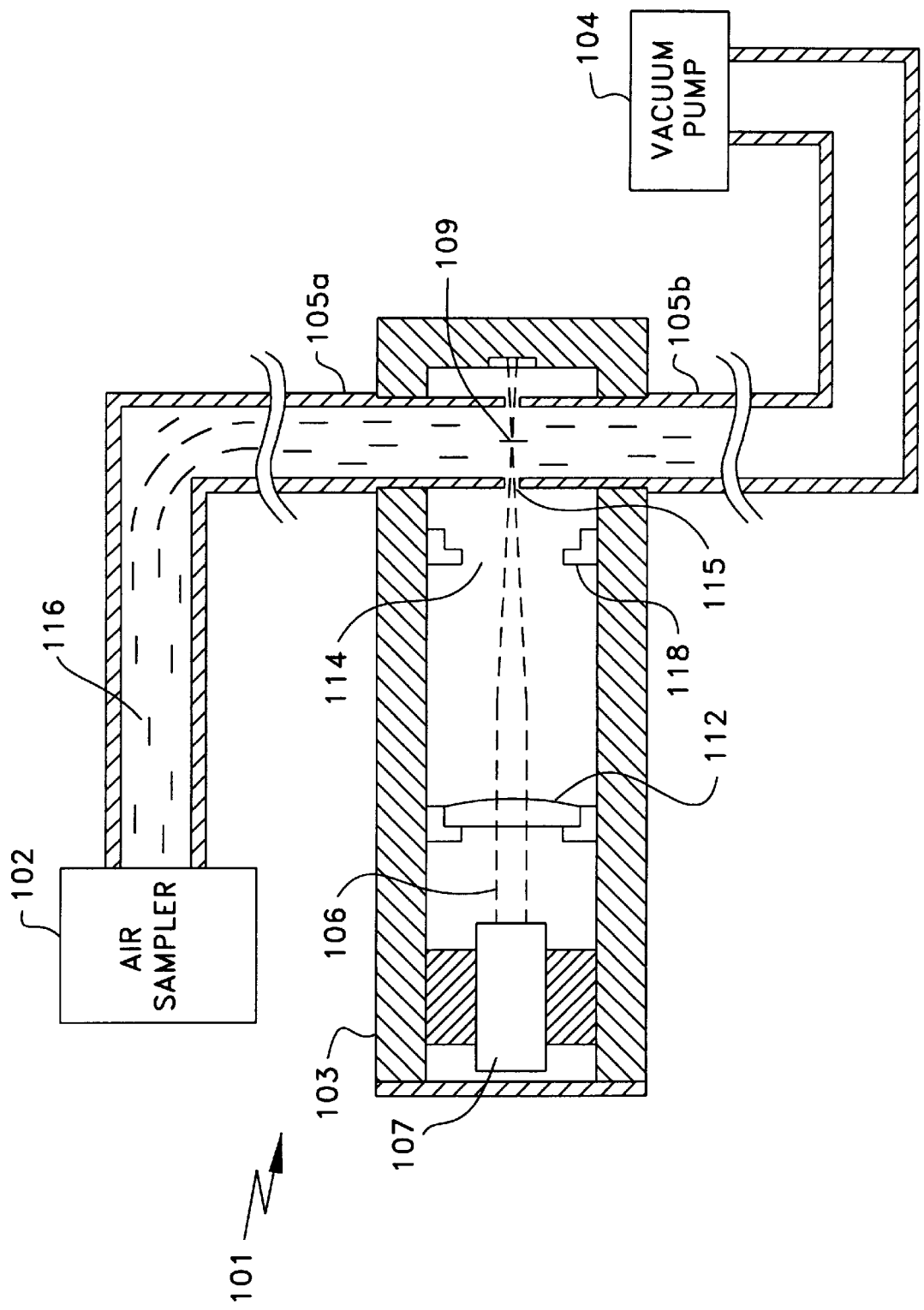
FIG. 5 is a top, cross-sectional illustration of the fiber diameter measuring device of FIG. 4.

FIG. 4 illustrates a cross-sectional view of another device 101 of this invention, sectioned in a plane generally perpendicular to the airflow. FIG. 5 illustrates a top view of the embodiment of FIG. 4, along the plane indicated by line 5—5. Referring to FIGS. 4 and 5, device 101 can include sensor 103; alone, or with air sampler 102, sensor 103, vacuum pump 104, and flow tubes 105a, 105b in combination. Air sampler 102 can be used to prefilter, or condition, the fiber-laden air 116, or may be merely a sampling conduit. Sensor 103 is preferred to be an electro-optical sensor which provides a collimated light beam 106 using light source 107. Light source 107 is preferred to be a laser diode. A suitable laser diode can be, for example, a model LPM03(670-5) laser diode from Power Technology, Inc., Little Rock, Ark.

When collimated light beam 106 strikes airborne fiber 109, for example a cylindrical glass fiber, scattered light 108 is produced. It may be desirable to provide a light beam 106 with a preselected cross-section along the path of beam 106, for example, an narrow elliptical cross-section. A portion of scattered light 108 is detected by light sensor 110, which can be a photodetector. A suitable photodetector is, for example, Devar Model 509-10, Bridgeport, Conn.

Unlike prior art devices, which directly measure the amount of light remaining in a beam after impinging upon a fiber particle, this invention employs the characteristics of scattered light 108 as sensed by photodetector 110 and analyzed by dimension measuring circuit 111.

In operation, vacuum pump 104 is attached to one end of flow tube 105b, and draws fiber-laden air 116 through tubes 105a, 105b. The flow rate of air 116 is chosen such that the flow in tubes 105a, 105b is laminar in nature. Also, the lengths of tubes 105a, 105b are chosen such that there is a sufficient distance for the laminarly-flowing, fiber-laden air 116 to align the longitudinal axis of fiber 109 with the direction of the airflow. With reference also to FIG. 5, it is preferred that a small gap 115 be formed between tubes 105a, 105b to permit collimated beam 106 to pass therethrough. Gap 115 can be used as a beam-steering device to preferentially direct scattered light 108 having the preselected orientation to sensor 110.

In general, when fiber 109 enters the path of laser beam 106, light is scattered. If fiber 109 is aligned with the flow of air 116, then its longitudinal axis will be substantially perpendicular to laser beam 106 thus scattering light into a plane normal to the axis of tubes 105a and 105b (best seen in FIG. 1). The portion of scattered light 108 having this preselected orientation can be collected by lens assembly 113 and focused onto photodetecter 110 producing a measuring signal 117, the characteristics of which are indicative of the dimensions of fiber 109.

Signal 117 can be processed by dimension measuring circuit 111, which can produce a perceptible representation of the dimensions of fiber 109. Responsive to scattered light 108, photodetector 110 generates a voltage, the duration of which is essentially a function of the length and velocity of fiber 109, and the thickness of beam 106. If the thickness of beam 106 and the velocity of fiber 109 are substantially fixed, the length of the fiber 109 can be determined by measuring, for example, the duration of signal 117.

The amplitude of signal 117 typically depends upon: (1) the wavelength of beam 106 and its intensity at the location of fiber 109; (2) the diameter of fiber 109; and (3) the angles over which scattered light 108 is collected. It is preferred that the wavelength of the light source and the light collection angles be fixed by the design of the system. It also is desirable to keep the intensity of beam 106 substantially constant in the region in which fibers 109 might be detected. Thus, the voltage amplitude of signal 117 can be made to depend primarily on the diameter of fiber 109.

For ease of analysis, it is desired that the dependency of the voltage amplitude of signal 117 upon fiber dimensions be both linear and monotonic. However, where linearity is difficult or impossible to achieve, dependency can nevertheless be determined by an approximately monotonic signal. This signal can be provided by collecting scattered light 108 over a preselected range of collection angles.

As an example, for a light wavelength of about 670 nm, it is preferred to collect light from about 60° to about 120° relative to the direction of laser beam 106, thus producing an approximately monotonic voltage amplitude range, which is indicative of the diameter of a small fiber 109 of less than about 10 microns or so. Furthermore, it is preferred that beam 106 from light source 107 be very thin to simplify the measurement of the length of fiber 109, although, even where the length of fiber 109 is generally less than the thickness of beam 106, fiber lengths can still be measured.

It is preferred that a laser diode be used as light source 107 because it typically produces an inherently thin, oval-shaped beam 106. It is preferred that light source 107 be oriented such that the wide dimension of beam 106 is generally perpendicular to the flow of air 116 and that fiber 109 passes through the thin dimension of beam 106. To further minimize the thickness of beam 106, a focusing lens 112, for example, a cylindrical lens, can be used. One advantage of cylindrical lens 112 is that the width of beam 106 is not operatively reduced thereby.

In general, the beam intensity across the width of beam 106 is approximately Gaussian. Therefore, it is preferred to place beam block 118, having aperture 114 therein, in the path of beam 106 to substantially block low-intensity edges of beam 106. Typically, Fresnel diffraction can occur from the edges of aperture 114. Although this diffraction cin cause some ripple in the intensity across the width of the remaining beam 106, the "bright edge" associated with this diffraction helps to raise the intensity where the Gaussian intensity curve otherwise would be falling. Thus, the intensity across the width of beam 106 is nearly constant with some ripple.

As stated previously, existing prior art devices typically analyze the amount of light directly received from the light source, as affected by the passage of an airborne fiber through the light beam. The present invention preferably does not analyze direct light signals, but rather, scattered light signals having a preselected orientation after striking the fiber.

Figure 6:
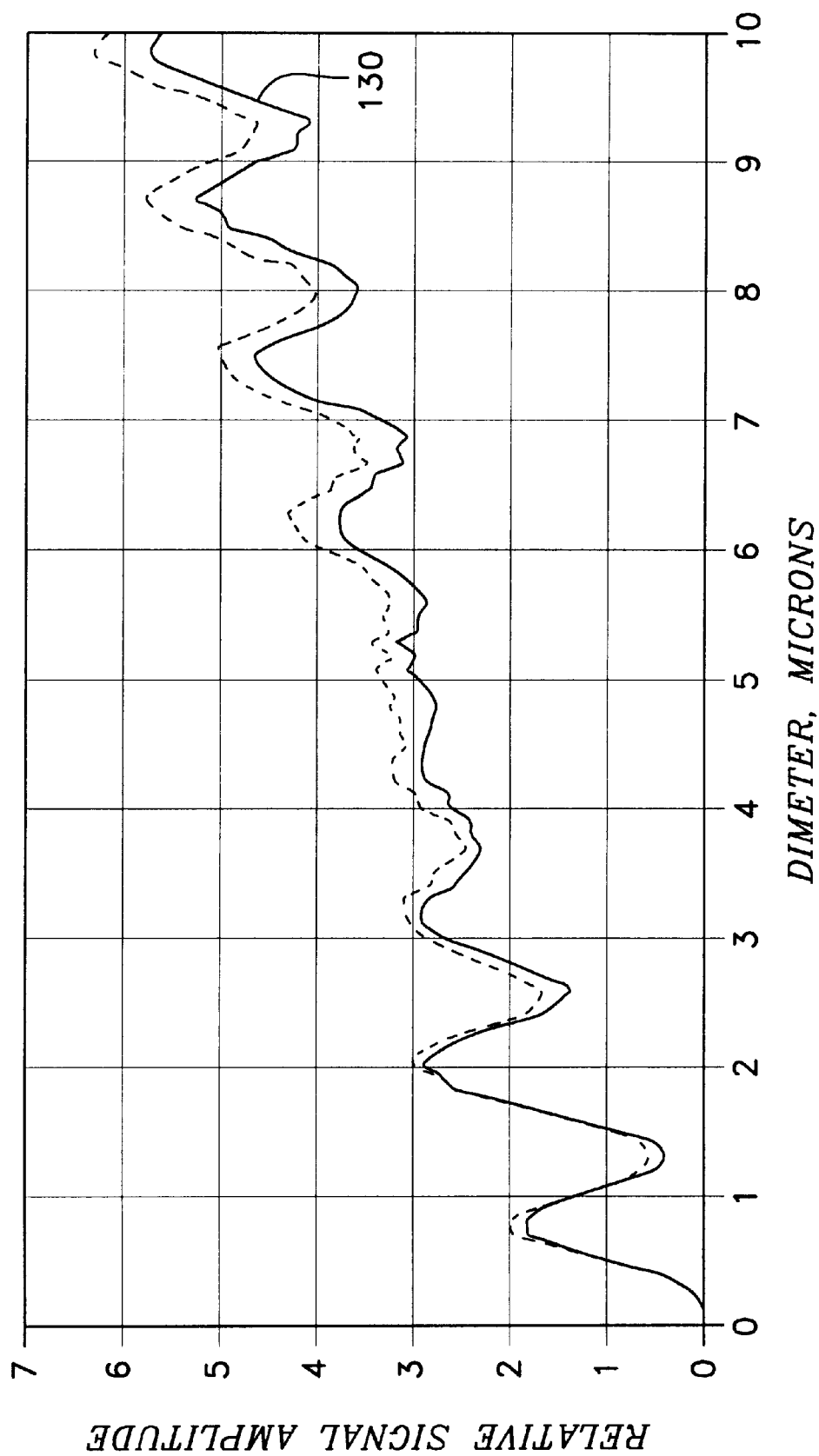
FIG. 6 is a graphical illustration of a light sensor amplitude vs. fiber diameter generated in response to a detected forward scattered light.

The advantages of this approach can be better appreciated by examining the response of a photodetector to directly impinging light as a function of fiber diameter and the light beam being attenuated by fibers, as seen in FIG. 6. Response curve 130 arises from the direct impingement of a collimated light beam upon a photodetector as a function of fiber diameter. Response curve 130 is neither linear nor monotonic and may not reliably produce a signal that is representative of fiber diameter.

Figure 7:
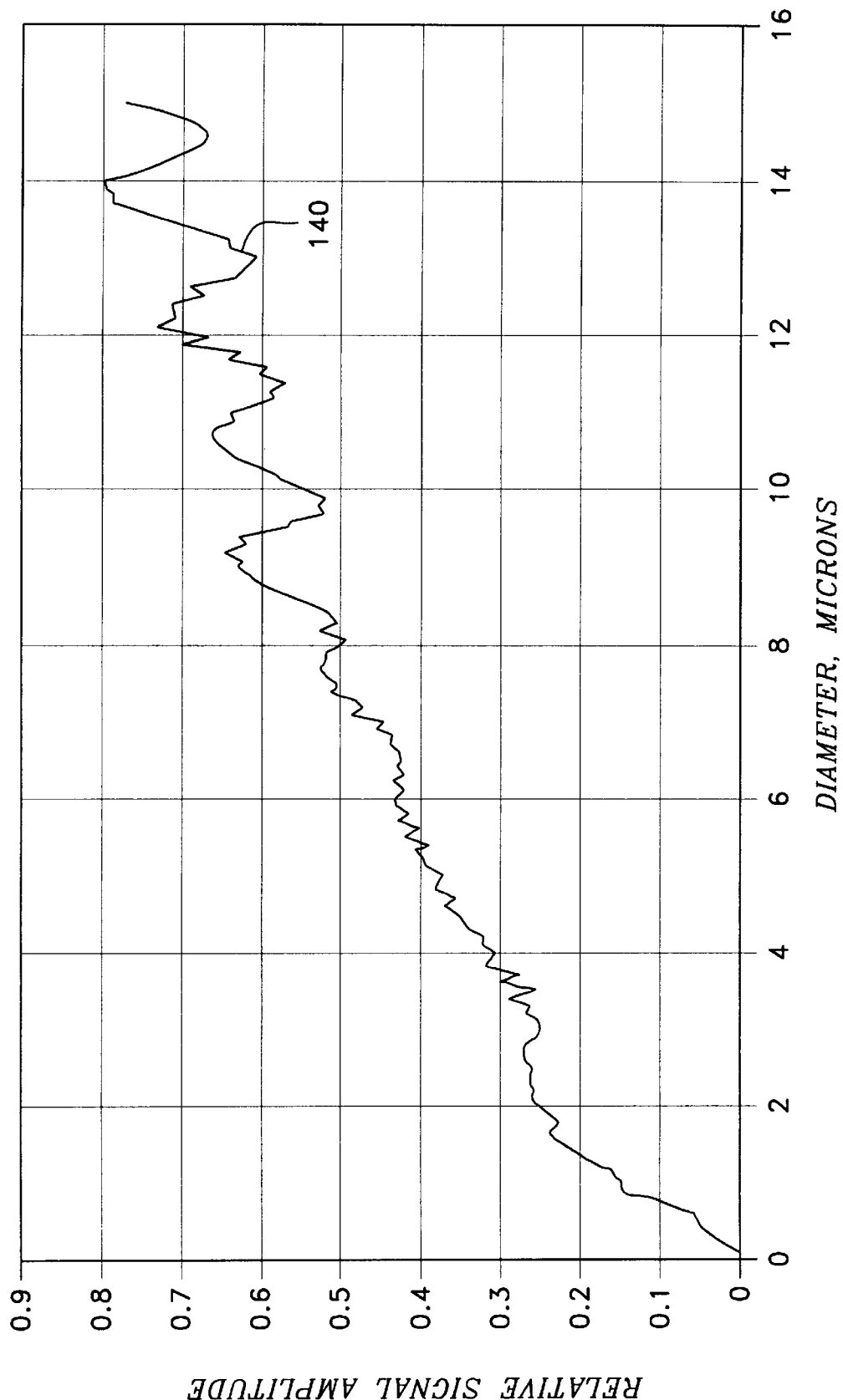
FIG. 7 is a graphical illustration of a light sensor amplitude vs. fiber diameter generated in response to a light scattered laterally from the bean path at about 60° to 120°.

However, when scattered light 108 having a preselected orientation is used to determine fiber diameter, the photodetector response can be made approximately monotonic over a predetermined range, as seen with response curve 140 in FIG. 7. The approximate monotonicity of response curve 140 is associated with fiber sizes below about 8–10 microns, and especially below about 9 microns, using a light wavelength of about 670 nm. A skilled artisan would recognize that light at other wavelengths may be desirable for fibers of other diameters. In general, the shorter the light wavelength, the narrower the dimension of the fibers that can be accurately determined.

Two linear approximations can be applied over the monotonic range of curve 140 to better estimate the response. For example, one linear approximation can be employed for fiber diameters of up to about 2 microns and a second linear approximation may be used for fiber diameters between about 2 microns and about 8 microns.

In preferred embodiments of the present invention, the scattered light 108 sensed by light sensor 110 and its lens 113 are preferred to be at a preselected orientation of between about 60° and about 120° relative to the beam path.

Improved Fiber Concentration Measurements Using Voltage Threshold Screening

Figure 8:
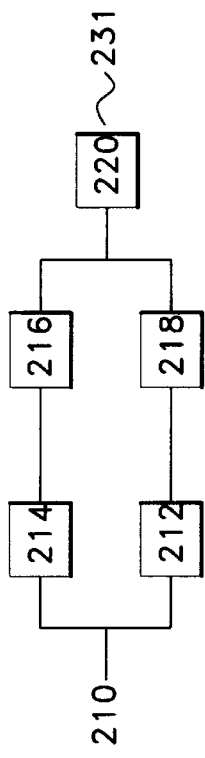
FIG. 8 is a schematic illustration of a preferred measurement circuit.

This invention also provides an improved fiber concentration measuring device, with an improved first embodiment measurement circuit 231, shown in FIG. 8.

Figure 9:
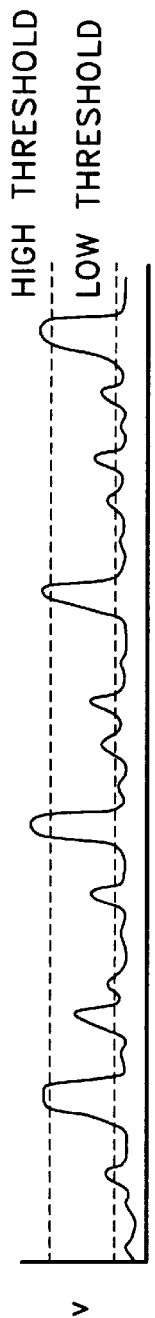
FIG. 9 is a graphical illustration of photo detector signals vs. time showing high and low voltage thresholds representing large and small diameter fibers respectively.

The photodetector signal 210 is sent to two voltage comparator circuits, a low threshold comparator circuit 212 and high threshold comparator circuit 214, which are preferably arranged in parallel. The two circuits 212 and 214 have different voltage ("v") threshold levels as shown in FIG. 9. When the voltage at the input of a comparator exceeds the threshold .he output goes from a low level to a high level, registering a pulse. The outputs of the comparators are sent to pulse counting circuits 216 and 218. When a signal goes from low to high the pulse counter increments the count that it has stored in it.

The counts stored in the counter 218 connected to the comparator with the low threshold 212 represent all fibers counted while the counter 216 for the high threshold comparator 214 represents the large non-respirable fibers. Given these counts, the air flow rate and the period of time ("t") in which the counts were accumulated, the calculating unit 220 can compute the concentration of all fibers, non-respirable fibers and respirable fibers. In practice the counter circuits 216 and 218 and calculating unit 220 could be parts of a general purpose microprocessor server or personal computing device.

Figure 10:
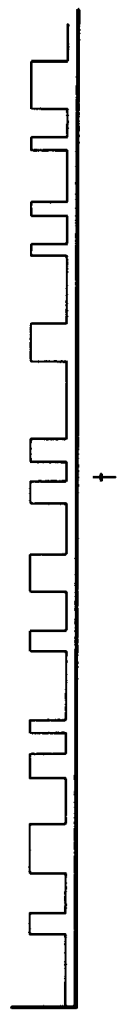
FIG. 10 is a graphical illustration of the output of the low threshold comparator circuit vs. time.
Figure 11:
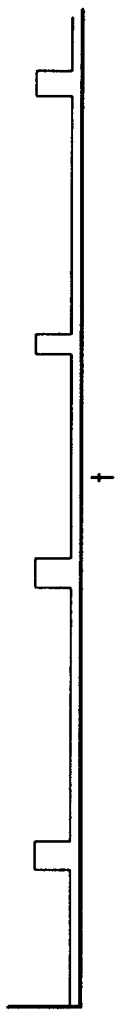
FIG. 11 is the output of the preferred high threshold comparator circuit vs. time.

FIGS. 9–11 represent graphs of simulated signals from the photodetector and the two comparator circuits 212 and 214 for the photodetector signal 210. Note that when the photodetector voltage exceeds one of the thresholds, the output of the corresponding comparator goes high. The output of comparator 212 is shown in FIG. 10 and the output of comparator 214 is shown in FIG. 11. This occurs 13 times for the low threshold and four times for the high threshold in FIG. 9. Hence during the time ("t") covered by these graphs the measurement circuit 231 would have reported detecting 13 fibers total, the counts in FIG. 10., of which 4 were non-respirable and 9 were respirable. Given the flow rate and the time represented by these graphs the concentration of fibers could be computed.

All publications mentioned in this specification are indicative of the level of skill of the skilled in the art to which this invention pertains. All publications are herein incorporated by reference to the same extent as if each individual publication was specifically but individually indicated to be incorporated by reference.

While specific embodiments of practicing the invention have been described in detail, it will be appreciated by those skilled in that art that various modifications; and alternatives to those details could be developed in light of the overall teachings of the disclosure. Indeed, a skilled artisan would recognize that, although the invention has been described in terms of determining the concentration of airborne respirable fibers, the apparatus and method illustrated in detail herein also can be used to detect, characterize, and visualize other types of particles having specific optical properties. Accordingly, the particular arrangements of the methods and apparatus disclosed are meant to be illustrative only and not limiting to the scope of the invention, which is to be given the full breadth of the following claims, and my and all embodiments thereof.

What is claimed is:

1. A device for measuring the concentration of respirable airborne fibers in a fiber-containing air sample, said device comprising:
    a. flow means for providing laminar flow to at least a portion of the fibers in said air sample;
    b. a flow channel for receiving a plurality of laminarly flowing fibers, the fibers moving along plural paths in said flow channel;
    c. a light source for generating a light beam directed to said plurality of laminarly flowing fibers to produce scattered light; and
    d. a light sensor for sensing a portion of said scattered light and for generating an output from which a respirable fiber concentration estimate in said air sample can be measured.

2. The device of claim 1, wherein the sampled air also includes non-respirable fibers and non-fibrous particulate matter therein.

3. The device of claim 1, wherein said device has a slotted opening for channeling scattered light to said light sensor.

4. The device of claim 1, wherein said light source includes collimation means for providing a light beam having a preselected cross-section along a beam path.

5. The device of claim 4, wherein said flow channel has a longitudinal axis which is substantially normal to the beam path.

6. The device of claim 3, wherein said slotted opening is disposed to screen out scattered light which does not have a preselected orientation to the light sensor.

7. The device of claim 6, further including an optical lens for receiving a portion of the scattered light having a preselected orientation and for directing at least a portion of this scattered light to the light sensor.

8. The device of claim 7, further including a beam block located in a path of said light beam, said beam block being umbrageously situated relative to the light sensor, the beam block substantially blocking the light beam from the light sensor.

9. The device of claim 1, wherein said light sensor includes means for generating a first light pulse having a first amplitude which is representative of a respirable fiber and a second pulse having second amplitude which is representative of a particle which is not a respirable fiber, said device capable of discriminating between the first amplitude for said respirable fiber and the second amplitude for said particle, and providing a signal which is representative of a concentration of respirable fibers.

10. The device of claim 9, wherein said particle is a non-respirable fiber.

11. A method of measuring the concentration of airborne fibers in a fiber-containing air sample containing respirable and non-respirable fibers, characterized by:
    a. providing laminar flow to at least a portion of the fibers in said air sample, said portion containing respirable and non-respirable fibers;
    b. directing a light beam at said laminarly flowing respirable and non-respirable fibers, said fibers flowing on plural paths, to produce a scattered light; and
    c. sensing a portion of said scattered light and generating an output from which a respirable fiber concentration estimate can be produced.

12. The method of claim 11 wherein said sensing step includes providing first and second pulse signals corresponding to the detection of light from a respirable and a non-respirable fiber respectively, said first and second pulse signals having first and second amplitudes, said method further including discriminating between said first and second amplitudes to provide a signal representative of a concentration of respirable fiters in said air sample.

13. The method of claim 11 wherein said directing step (b) comprises directing a collimated laser light at said laminarly flowing respirable and non-respirable fibers to produce a scattered light.

14. The method of claim 11 wherein said sensing step (c) comprises comparator circuit means for differentiating between photodetector signals for respirable and non-respirable fibers.

15. The method of claim 14 wherein said sensing step (c) comprises subtracting pulses representative of photodetector signals for non-respirable fibers from pulses generated for all non-respirable and respirable fibers to provide an output signal indicative of a concentration of respirable fibers.

16. A device for measuring the concentration of a respirable airborne fiber in a fiber-containing air sample, said device comprising:
(a) flow means for providing laminar flow to at least a portion of the fibers in said air sample;
(b) a flow channel for receiving a plurality of laminarly flowing fibers;
(c) a light source for generating a light beam directed to said plurality of laminarly flowing fibers to produce scattered light;
(d) a photodetector for sensing a portion of the scattered light and for producing a photodetector outlet signal; and
(e) measurement circuit means for receiving said photodetector output signal and for generating pulse counts representative of a number of said respirable fibers in said air sample.

17. The device of claim 16 wherein said measurement circuit means comprises a pair of voltage comparator circuits including a low threshold comparator and a high threshold comparator, said low threshold and said high threshold comparator arranged in parallel.

18. The device of claim 17 wherein said low threshold comparator and said high threshold comparator generate a first pair of outputs which are sent to a first and a second pulse counting circuit respectively.

19. The device of claim 18 wherein said first and second pulse counting circuits generate first and second pulse outputs representative of a concentration of all fibers in said air sample and a concentration of non-respirable fibers in said air sample.

20. The device of claim 19 further comprising computation means for determining a concentration of respirable fibers in said air sample based upon the first and second pulse outputs and a flow rate for said plurality of laminarly flowing fibers.

* * * * *